United States Patent [19]

Farrish et al.

[11] 3,962,381

[45] June 8, 1976

[54] HUMIDIFICATION APPARATUS

[75] Inventors: Dean T. Farrish, Parker; Dalton E. Templeton, Denver, both of Colo.

[73] Assignee: Sandoz, Inc., E. Hanover, N.J.

[22] Filed: Nov. 11, 1974

[21] Appl. No.: 522,528

[52] U.S. Cl. .......... 261/141; 261/123; 261/151; 261/DIG. 65

[51] Int. Cl.[2] .......... G01D 18/00; A61M 16/00

[58] Field of Search .......... 261/151, 152, 141, 122, 261/123, DIG. 65, DIG. 28; 128/192, 193, 194

[56] References Cited

UNITED STATES PATENTS

| | | | |
|---|---|---|---|
| 1,795,328 | 3/1931 | Brown | 128/192 |
| 2,116,328 | 5/1938 | Silten | 128/192 |
| 3,714,392 | 1/1973 | Katzman et al. | 128/192 |
| 3,743,780 | 7/1973 | Camp | 128/192 |
| 3,769,162 | 10/1973 | Brumfield | 261/DIG. 28 |

*Primary Examiner*—Frank W. Lutter
*Assistant Examiner*—Gregory N. Clements
*Attorney, Agent, or Firm*—Gerald D. Sharkin; Robert S. Honor; Walter F. Jewell

[57] ABSTRACT

This invention relates to an apparatus for the humidification of a gas, and it comprises an outer container having an inner chamber and a top cover. Within the inner chamber is a helix-shaped gas bubble conveyer. Water is introduced into the container, which in turn, fills the chamber. Gas bubbles are introduced into the chamber, and as they traverse the helix pathway, they are saturated with the water. Means are provided for recirculating the water and maintaining it at any desired temperature.

17 Claims, 2 Drawing Figures

HUMIDIFICATION APPARATUS

This apparatus relates to humidification. More particularly, it relates to the humidification of callibrating gas, i.e., air, for use in Blood Gas Analyzers.

In operation of a Blood Gas Analyzer, it is necessary to humidify the callibrating gas. Since the ability of the gas to gain moisture is proportional to its time in contact with water, either a large path length, or a long emmersion time must be provided to fully humidify the gas.

It is, therefore, an object of this invention to provide an apparatus having a large gas path through a humidifying liquid in a relatively confined space.

Figure 1:
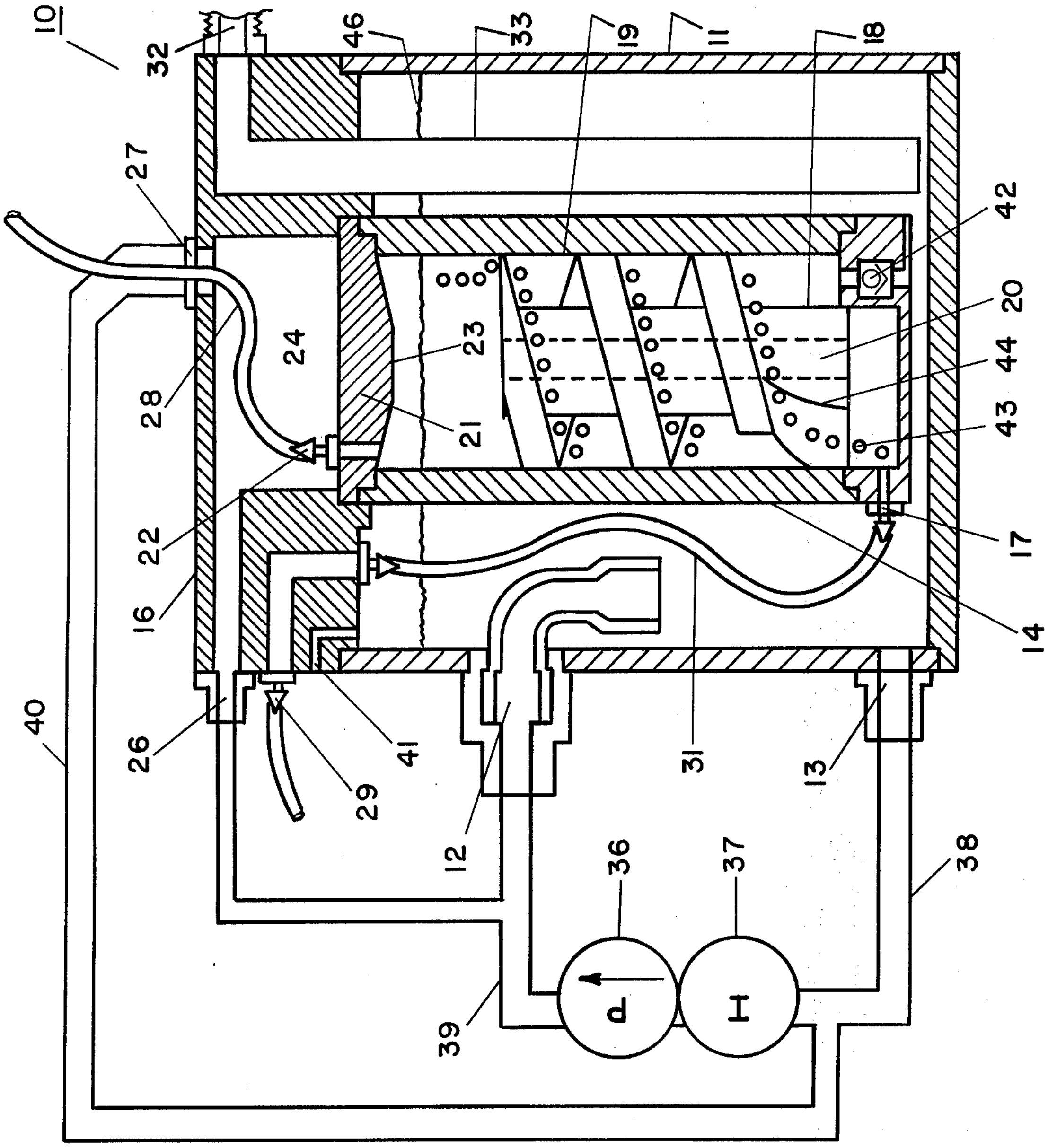
Figure 2:
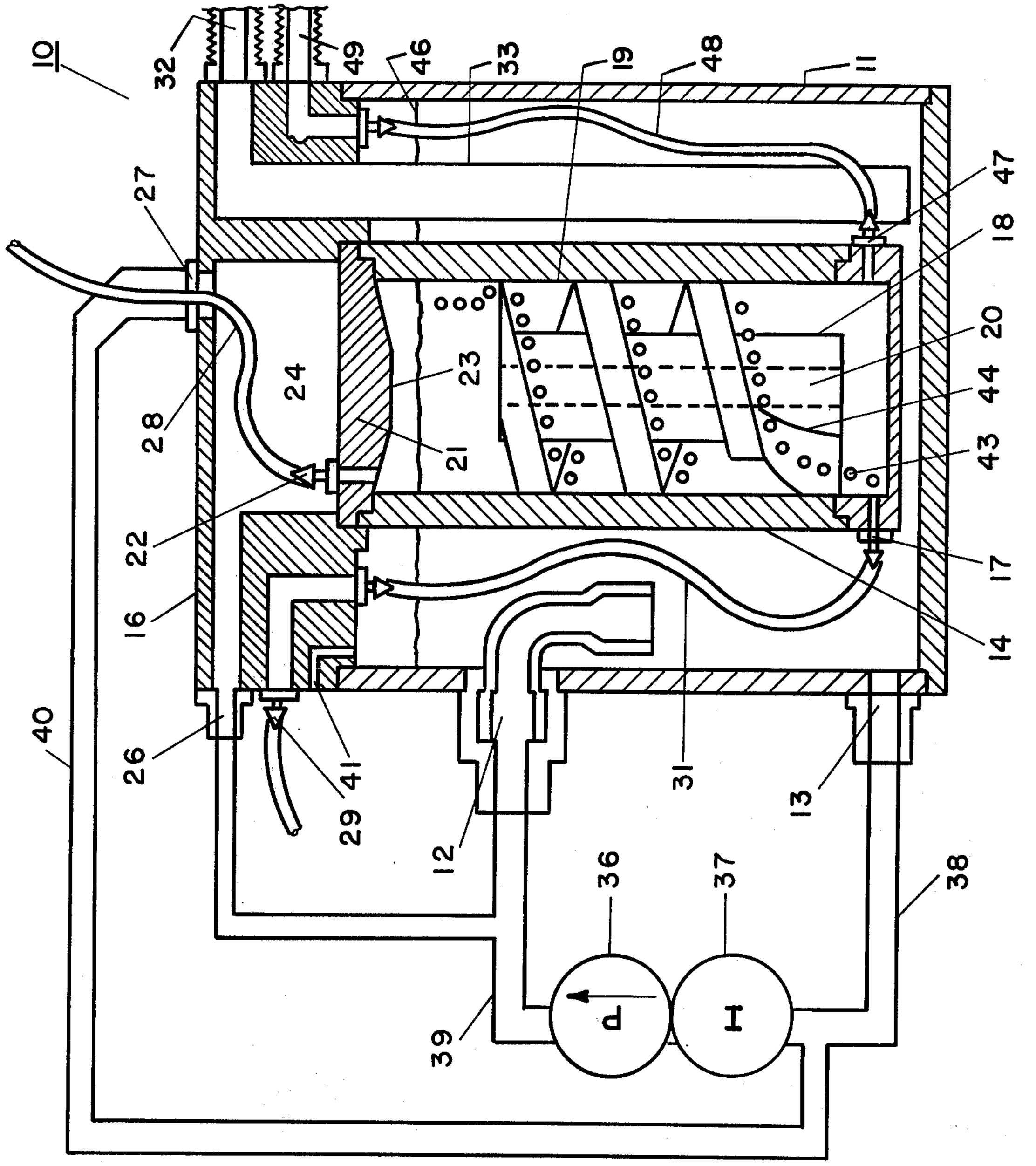

This and other objects of the invention will be understood from the following detailed description and drawing, wherein;

FIG. 1 is a cross-sectional view of a humidification apparatus of this invention, and FIG. 2 is a cross-sectional view of the humidification of FIG. 1 showing a preferred embodiment.

Broadly, this invention provides an apparatus for the humidification of a gas, and it comprises, in combination, an outer container, an inner chamber, and a top cover.

The outer container is provided with a liquid, e.g., water, recirculation means for circulating the liquid from a heating bath through the container. The inner chamber has a gas inlet means, which releases gas bubbles onto a helixal-shaped gas conveying means releasing the gas through a gas outlet, and thus into the Blood Gas Analyzer. The helixal-shaped gas conveying means is provided with an axial liquid there through for conveying through the chamber. The chamber is provided with a one-way valve which emits water from the container into the chamber to maintain a constant water level. A feature of the chamber is a convex inner surface at the top, which forms a bubble trap to prevent any water carry-over into the gas stream as it exits the chamber.

The top of the apparatus is in a sealable engagement with both the outer container and the inner chamber. The top contains a liquid chamber through which the exiting gas passes, via a water tight conduit. Water is circulated through this chamber to maintain the gas at the proper temperature, prior to exiting from the apparatus. The gas conduit is in pass-through communication with the water outlet. The gas is thus conveyed through the top cover to a Blood Gas Analyzer.

A conduit is communicatively connected to the gas inlet in the top cover and the gas inlet of the chamber and passes through the water in the container.

It is a feature of this invention that the inner chamber be suspended from the top cover, thus creating a space between the bottom of the chamber and the base of the container.

It is an additional feature of this invention that the helixal-shaped conveying means have an appendage at its lower end, which appendage is situated such that gas entering the chamber is immediately conveyed up the helixal passageway.

It is also a feature of this invention that the appendage of the conveying means supports the conveying means in a spaced-apart relationship with the base of the chamber. It is a further feature of the invention that the appendage is set to one side of the chamber gas inlet means such that the gas bubbles from the inlet are directly conveyed by the appendage to the helixal pathway.

The apparatus is further provided with an air vent, which communicates with the atmosphere and interior of the container through the top cover. The apparatus also provides means for filling or draining the liquid in the container and chamber.

In operation, gas enters the gas inlet in the top cover and is conveyed, via a flexible conduit through the recirculating liquid in the container and into the chamber, where the gas bubbles are directed up through the helixal passageway and through the liquid chamber in the top cover; and hence, to the gas analyzer. The temperature of the liquid, and hence, the gas is maintained at the desired degree by recirculating the liquid through a heater means. The one-way valve in the base of the chamber prevents liquid outflow from the chamber, but allows liquid to enter the chamber as the level is depleted by the humidification of the gas.

Should the apparatus of this invention be used in systems requiring a constant back-pressure on the gas system, difficulties may be encountered in maintaining the liquid level in the chamber, via the one-way valve. Gas back-pressure may prevent the operation of the one-way valve. When such conditions arise, it is a preferred embodiment of the invention that the liquid level in the chamber may be maintained by sealing the one-way valve and introducing liquid into the chamber, via a liquid inlet means communicating with the inner chamber.

The apparatus of this invention will be best understood from the following detailed description:

There is shown in FIG. 1, generally, at 10 a humidification apparatus of this invention having an outer container 11, a liquid, e.g., water, intake 12, and a water outflow 13. A chamber 14 is affixed to a top cover 16 and has a gas inlet 17 and a helixal-shaped gas bubble conveying means 18, which is in gas-liquid tight communication with the interior wall 19 of chamber 14. The bubble conveying means 18 has an axial liquid conduit 20 through it for water movement within the chamber 14. The top portion 21 of the chamber 14 has a gas exiting port 22 and a convex inner surface 23. The top portion 21 of the chamber 14 forms the base of a liquid chamber 24 within the top cover 16. A water inlet 26 and a water outlet 27 are in communication with the liquid chamber 24. The gas is conveyed through the chamber 24, via a conduit 28, which conduit is in pass-through relationship with the water outlet 27.

Gas enters the apparatus 10, via an inlet port 29 in the top cover 16, and this port communicates with a conduit 31, which conveys the gas to the inlet port 17 in the chamber 14. The apparatus 10 is filled with water, via a liquid inlet 32, which communicates with the interior of the container 11, via a conduit 33. This conduit terminates above the base of the container 11. The liquid intake 32 may be closed by means of a cap or by other means known to the art. The liquid intake port 12 and outflow port 13 in the container are in communication with a pump 36 and a heater 37, via conduits 38 and 39. The apparatus is provided with an air vent 41, which is in communication with the atmosphere and the interior of the container 11.

The base of the inner chamber is in a spaced-apart relationship with the base of the container and is provided with a one-way valve 42, (see FIG. 1), which allows liquid from the container 11 to flow into the chamber 14, but prevents any outflow of the liquid from the chamber into the container.

In operation, gas, i.e., air, enters the apparatus 10, via the gas intake port 29 and traverses conduit 31 to the intake port 17 of the chamber 14. The gas enters the chamber 14 in the form of bubbles 43 and is guided by the appendage 44 on the helixal means 18 up to the hexial pathway. The bubbles are released above the liquid level 46 and are trapped by the convex surface 23 of the top portion 21 of the chamber. This bubble trap prevents any liquid carry-out from the chamber. The gas exits the chamber, via port 22 and is conveyed through conduit 28 through the circulating liquid in the chamber 24 and out through the liquid exit port 27 to the Blood Gas Analyzer.

The liquid in the apparatus is maintained at any desired temperature by recirculating it through the heater 37 by means of a pump 36. Conduits 38, 39 and 40 convey the liquid on its recirculation path.

The apparatus 10 may be easily filled with liquid by means of a liquid port 32 and may also be drained of liquid through the same port.

Water is conveniently conveyed through the chamber 14 by means of the axial liquid conduit 20 through the helixal means 18.

As noted above, when the apparatus of this invention is used in a system where a constant back-pressure is maintained on the gas system, the water level in the chamber 14 may be maintained, via a liquid port 47 and conduit 48, which is in flow communication with a liquid inlet port 49, (see FIG. 2). The chamber may also be drained of liquid through the same port. The liquid port 49 may be closed by means of a cap or other means known to the art.

In a further embodiment of this invention, the entire apparatus may be emmersed in a controlled temperature, water bath, and the water recirculated through the apparatus by means of a pump.

What is claimed is:

1. An apparatus for the humidification of a gas, which comprises in combination:
   a. An outer container having liquid recirculation means;
   b. An inner chamber, having gas inlet and gas outlet means, a helixal-shaped gas conveying means in gas-tight communication with the inner wall of the chamber, having an axial liquid conduit there through, and adapted to convey gas bubbles upward in a helixal pathway through a liquid in the chamber, a one-way valve at the base of the chamber, communicating with the chamber and the outer container and adapted to maintain a pre-set liquid level in the chamber, a top portion for the chamber having said gas outlet means and a substantially convex inner surface adapted to form a bubble trap;
   c. A top cover in sealable engagement with the outer container and the inner chamber having a liquid chamber having liquid inlet means and liquid outlet means, conduit means in the liquid chamber in communication with the gas outlet means of the top portion of the inner chamber, the conduit means in pass-through communication with the liquid outlet means, a gas inlet means communicating with the inner chamber, and a liquid inlet means communicating with the outer container;
   d. A second conduit means in the outer container in communication with both the gas inlet means of the top cover and the gas inlet means of the inner chamber.

2. The apparatus according to claim 1, wherein the top portion of the inner chamber is in gas-liquid sealed relationship with the top cover, the top portion comprising the bottom section of the liquid chamber of the top cover.

3. The apparatus according to claim 2, wherein the inner chamber is suspended from the top cover and the bottom of the chamber is in spaced-apart relationship with the base of the outer chamber.

4. The apparatus according to claim 3, wherein the bottom of the gas conveying means is in communication with an appendage of the conveying means which supports the conveying means in spaced-apart relationship with the base of the chamber.

5. The apparatus according to claim 4, wherein the base of the appendage is set to one side of the chamber gas inlet means and adapted to convey the gas bubbles from the inlet directly to the helixal pathway.

6. The apparatus according to claim 5, wherein an air vent is in communication with the atmosphere air and the interior of the container.

7. The apparatus according to claim 6, wherein the liquid inlet means communicates with the interior of the container, via a conduit which is open to the container.

8. The apparatus according to claim 7, wherein pumping means and liquid heating means are in communication with the container.

9. An apparatus for the humidification of a gas, which comprises in combination:
   a. An outer container having liquid recirculation means;
   b. An inner chamber, having gas inlet and gas outlet means, a helixal-shaped gas conveying means in gas-tight communication with the inner wall of the chamber, having an axial liquid conduit there through, and adapted to convey gas bubbles upward in a helixal pathway through a liquid in the chamber, liquid inlet and outlet means adapted to maintain a pre-set liquid level in the chamber, a top portion for the chamber having said gas outlet means and a substantially convex inner surface adapted to form a bubble trap;
   c. A top cover in sealable engagement with the outer container and the inner chamber having a liquid chamber having liquid inlet means and liquid outlet means, conduit means in the liquid chamber in communication with the gas outlet means of the top portion of the inner chamber, the conduit means in pass-through communication with the liquid outlet means, a gas inlet means communicating with the outer container, a liquid inlet means communicating with the inner chamber, and a liquid inlet means communicating with the outer container;
   d. A second conduit means in the outer container in communication with both the gas inlet means of the top cover and the gas inlet means of the inner chamber.

10. The apparatus according to claim 9, wherein the top portion of the inner chamber is in gas-liquid sealed relationship with the top cover, the top portion comprising the bottom section of the liquid chamber of the top cover.

11. The apparatus according to claim 10, wherein the inner chamber is suspended from the top cover and the bottom of the chamber is in spaced-apart relationship with the base of the outer chamber.

12. The apparatus according to claim 11, wherein the bottom of the gas conveying means is in communication with an appendage of the conveying means which supports the conveying means in spaced-apart relationship with the base of the chamber.

13. The apparatus according to claim 12, wherein the base of the appendage is set to one side of the chamber gas inlet means and adapted to convey the gas bubbles from the inlet directly to the helixal pathway.

14. The apparatus according to claim 13, wherein an air vent is in communication with the atmosphere air and the interior of the container.

15. The apparatus according to claim 14, wherein the liquid inlet means communicates with the interior of the container, via a conduit which is open to the container.

16. The apparatus according to claim 15, wherein the liquid inlet means communicates with the interior of the chamber, via a conduit which is open to the chamber.

17. The apparatus according to claim 16, wherein pumping means and liquid heating means are in communication with the container.

* * * * *